US011191527B2

(12) United States Patent
Igarashi et al.

(10) Patent No.: US 11,191,527 B2
(45) Date of Patent: Dec. 7, 2021

(54) ULTRASONIC DIAGNOSTIC APPARATUS AND PROBE USED FOR THE SAME

(71) Applicant: Hitachi, Ltd., Tokyo (JP)

(72) Inventors: Yutaka Igarashi, Tokyo (JP); Shinya Kajiyama, Tokyo (JP); Yohei Nakamura, Tokyo (JP); Kengo Imagawa, Tokyo (JP); Kazuhiro Amino, Tokyo (JP); Takayuki Iwashita, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 279 days.

(21) Appl. No.: 16/361,858

(22) Filed: Mar. 22, 2019

(65) Prior Publication Data
US 2019/0328369 A1 Oct. 31, 2019

(30) Foreign Application Priority Data

Apr. 27, 2018 (JP) .............................. JP2018-086644

(51) Int. Cl.
*A61B 8/00* (2006.01)
*B06B 1/02* (2006.01)
(Continued)

(52) U.S. Cl.
CPC .............. *A61B 8/54* (2013.01); *A61B 8/4488* (2013.01); *A61B 8/56* (2013.01); *B06B 1/0223* (2013.01);
(Continued)

(58) Field of Classification Search
CPC ... A61B 8/4405; A61B 8/4488; A61B 8/5207; A61B 8/54; A61B 8/56; B06B 1/0223;
(Continued)

(56) References Cited

U.S. PATENT DOCUMENTS

2002/0055341 A1* 5/2002 Otaka ................. H03F 3/45183
455/200.1
2003/0038740 A1* 2/2003 Mulder ............ H03K 17/04106
341/144
(Continued)

FOREIGN PATENT DOCUMENTS

CN 1918790 A 2/2007
CN 101677802 A 3/2010
(Continued)

OTHER PUBLICATIONS

Chinese-language Office Action issued in Chinese Application No. 201910222493.6 dated Aug. 26, 2021 (11 pages).

*Primary Examiner* — Joanne M Hoffman
*Assistant Examiner* — Alexei Bykhovski
(74) *Attorney, Agent, or Firm* — Crowell & Moring LLP (57) ABSTRACT

Provided is a probe which transmits an ultrasonic wave to a diagnostic site and receives a reception signal which is a reflected wave. The probe includes: a plurality of transducers; a plurality of low-noise amplifying circuits respectively corresponding to the plurality of transducers; and a single differential converter which converts a control signal rising with the elapse of time to a first bias signal rising with the elapse of time and a second bias signal falling with the elapse of time to control the plurality of low-noise amplifying circuits, and the low-noise amplifying circuit includes an attenuator which attenuates: an electric signal from the transducer; a first amplifying circuit which sets the first bias signal as a bias and amplifies an output signal of the attenuator to be gradually increased with the elapse of time; a second amplifying circuit which sets the second bias signal as a bias and amplifies the output signal of the attenuator to be gradually reduced with the elapse of time; and a subtrac-
(Continued)

tor which subtracts an output of the first amplifying circuit and an output of the second amplifying circuit.

15 Claims, 8 Drawing Sheets

(51) Int. Cl.
    *B06B 3/00*       (2006.01)
    *H03F 3/45*       (2006.01)

(52) U.S. Cl.
    CPC ........... *B06B 3/00* (2013.01); *H03F 3/45188* (2013.01); *H03F 3/45273* (2013.01); *H03F 2200/294* (2013.01)

(58) Field of Classification Search
    CPC ... B06B 3/00; G10K 11/346; H03F 2200/294; H03F 3/45188; H03F 3/45273
    See application file for complete search history.

(56) References Cited

U.S. PATENT DOCUMENTS

| | | | |
|---|---|---|---|
| 2005/0057305 A1 | 3/2005 | Krone | |
| 2009/0231883 A1* | 9/2009 | Osaka | H02M 3/155 363/15 |
| 2012/0139633 A1* | 6/2012 | Nasu | H03F 3/195 330/254 |
| 2015/0207434 A1* | 7/2015 | Wang | H02M 7/483 363/78 |
| 2016/0249882 A1* | 9/2016 | Degertekin | A61B 1/05 600/424 |
| 2017/0163225 A1* | 6/2017 | Chen | A61B 8/4444 |
| 2018/0145682 A1* | 5/2018 | Foley | H03F 3/195 |
| 2018/0289361 A1* | 10/2018 | Ledoux | A61B 8/56 |

FOREIGN PATENT DOCUMENTS

| | | | | |
|---|---|---|---|---|
| CN | 106788280 A | | 5/2017 | |
| JP | 2004-8684 A | | 1/2004 | |
| JP | 2013188421 | * | 3/2012 | ............... A61B 8/00 |
| JP | 2013-188421 A | | 9/2013 | |

* cited by examiner

ULTRASONIC DIAGNOSTIC APPARATUS AND PROBE USED FOR THE SAME

BACKGROUND OF THE INVENTION

1. Field of the Invention

The present invention relates to an ultrasonic diagnostic apparatus.

2. Description of Related Art

A two Dimensional (D) array probe for an ultrasonic diagnostic apparatus is constituted of a 2D array transducer in which transducers are arranged two-dimensionally and a 2D array Integrated Circuit (IC) for driving the 2D array transducer. For the 2D array probe, the 2D array IC which enables transmission and reception from about 200 signal terminals is essential to the transducer array of several thousands to ten thousand elements. The 2D array IC controls the drive time of each transducer and manipulates a transmission and reception direction of an ultrasonic beam.

An individual transducer of the 2D array transducer and a transceiver circuit (hereinafter referred to as an "element channel circuit" or an ECh circuit) are connected one to one. Also, a subchannel (hereinafter referred to as a "subchannel" or an SCh) bundled with N number of ECh circuits (N is a positive integer) is connected to a transmission/reception signal input/output cable one to one. The meaning of "bundled" will be explained below.

In order to focus ultrasonic beams transmitted and received from each transducer of the 2D array transducer to an arbitrary in-vivo diagnostic site, when it is assumed that an in-vivo speed of ultrasonic waves is uniform, the ECh circuit must give a delay time proportional to a distance between a focal point and an individual transducer of the 2D array transducer. A larger delay time is given to a transducer closer to the focal point and a smaller delay time is given to a transducer far from the focal point.

During reception, all ECh circuit output signals within one SCh are added. This is called a phasing addition. This added signal is output from the cable to the ultrasonic diagnostic apparatus. During transmission, the signal transmitted from the ultrasonic diagnostic apparatus is branched to all ECh circuits within one SCh and a delay time is given to a signal at each ECh circuit, and then the signal is output from each transducer. This is the meaning of "bundled".

The resolution of an ultrasound tomogram generated by processing the signals received from the 2D array probe depends on the size of one transducer and the size of, for example, 200 to 300 µm is required. The resolution of an ultrasound tomogram also depends on the delay time resolution that can be set by the delay circuit of the ECh circuit. The viewing angle of the ultrasonic tomogram depends on the maximum delay time that can be set by the delay circuit of the ECh circuit.

The 2D array probe is a system which transmits ultrasonic waves and receives reflected waves, and therefore, it is affected by strong sound pressure by reflection of bone or the like when an image of the part close to a body surface is acquired. When a reception system of the 2D array IC, particularly an initial stage low-noise amplifying circuit (LNA) is level-designed so as not to saturate even at the high sound pressure, the gain is small and the noise characteristics are deteriorated, and thus, the SNR of a deep image deteriorates. Therefore, in a normal ultrasonic diagnostic apparatus which is not a 2D array probe, a system which increases the gain in accordance with the elapse of time from the start of reception is used and this is called time gain control (TGC).

As background arts for realizing a TGC circuit, there are JP-A-2004-8684 and JP-A-2013-188421. JP-A-2004-8684 discloses a configuration where an ultrasonic diagnostic apparatus is constituted by including a ultrasonic wave probe, a transmission unit for transmitting an ultrasonic wave to an object via the ultrasonic probe, a reception unit for processing a reception signal received from the object via the ultrasonic probe, an image forming unit for generating an image based on the reception signal, and an image display unit for displaying an image, in which the reception unit is constituted by including intensity-dependent variable attenuation means in which a gain changes in response to the signal strength of the reception signal and time-dependent variable attenuation means in which the gain changes in accordance with the reception time of the reception signal. Further, in JP-A-2013-188421, the ultrasonic diagnostic apparatus includes a transmission unit for transmitting a ultrasonic signal to an object with a reception signal via an ultrasonic probe and a reception unit for processing a reception signal obtained by being reflected within the object, in which the reception unit includes a transmission/reception changeover switch portion for transmission/reception isolation that prevents the transmission signal from entering the reception unit, an amplification portion for amplifying the reception signal, and an attenuation portion disposed between the transmission/reception changeover switch portion and the amplification portion and attenuating the reception signal. Further, a configuration where the attenuation portion attenuates a reflection signal from a short distance that receives a signal of a large amplitude immediately after the end of the transmission and changes the attenuation amount from large to small as the reception time elapses so as not to attenuate a signal from a long distance having a small signal amplitude is disclosed.

In JP-A-2004-8684, a part of passive elements (resistor elements) which determine a gain of an amplifying circuit using an operational amplifier is changed to an FET to make it variable attenuation means, but there is a problem in that element variation is large. Also, it is not considered that the area on a semiconductor and the power consumption are extremely large to adopt the operational amplifier as the LNA of the 2D array IC.

JP-A-2013-188421 has an attenuation means at a front stage of the LNA, but generation of a control signal is input from an external circuit. Since a diode is used, there is a problem in that variation in attenuation degree of the variable attenuator is large. In addition, since an attenuation means of an output section of the LNA is unknown, there is a problem in that a variable gain range as a TGC is insufficient.

That is, the TGC circuit to be mounted in the 2D array probe requires LNAs each having one independent variable gain function for each transducer array of several thousands to ten thousand elements. However, in the configurations described in JP-A-2004-8684 and JP-A-2013-188421, it is not possible to minimize the gain variation of each LNA while giving the necessary variable gain function (30 dB or more) to several thousands to ten thousand LNAs. Therefore, it is not possible to realize a configuration for supplying a gain control signal to a large number of LNA groups arranged in a 2D array form (matrix form) and performing TGC control without increasing the area of each LNA.

SUMMARY OF THE INVENTION

An object of the invention is to provide an ultrasonic diagnostic apparatus which solves the problems described above and realizes a TGC circuit suitable for being mounted in a 2D array probe, and a probe used for the ultrasonic diagnostic apparatus.

In view of the related art and the problems described above, to give one example, the invention provides a probe used for an ultrasonic diagnostic apparatus which includes a probe for transmitting an ultrasonic wave to a diagnostic site and receiving a reception signal which is a reflected wave and obtains information necessary for diagnosis based on the reception signal, where the probe includes: a plurality of transducers; a plurality of low-noise amplifying circuits respectively corresponding to the plurality of transducers; and a single differential converter which converts a control signal rising with the elapse of time to a first bias signal rising with the elapse of time and a second bias signal falling with the elapse of time to control the plurality of low-noise amplifying circuits, and the low-noise amplifying circuit includes: an attenuator which attenuates an electric signal from the transducer; a first amplifying circuit which sets the first bias signal as a bias and amplifies an output signal of the attenuator to be gradually increased with the elapse of time; a second amplifying circuit which sets the second bias signal as a bias and amplifies the output signal of the attenuator to be gradually reduced with the elapse of time; and a subtractor which subtracts an output of the first amplifying circuit and an output of the second amplifying circuit.

According to the invention, it is possible to provide an ultrasonic diagnostic apparatus realizing a TGC circuit suitable for being mounted in a 2D array probe, and a probe used for the ultrasonic diagnostic apparatus.

DESCRIPTION OF EMBODIMENTS

Hereinafter, examples of the invention will be described with reference to the drawings.

EXAMPLE 1

Figure 1:
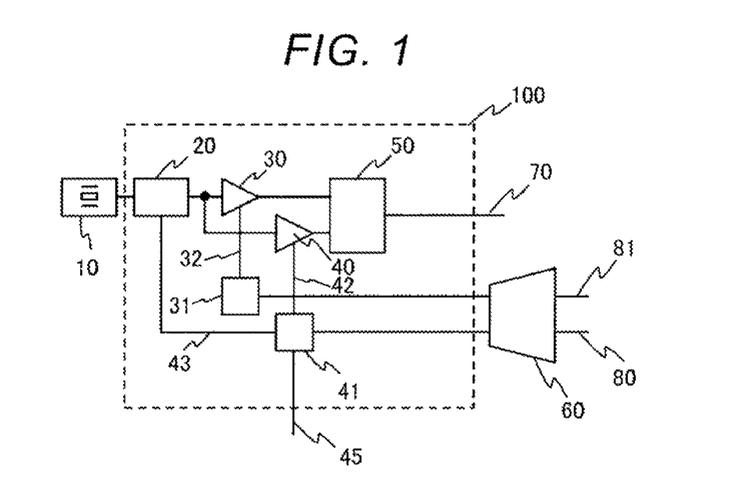
FIG. 1 is a block configuration diagram of an LNA and the periphery thereof in Example 1.

FIG. 1 is a block configuration diagram of an LNA and the periphery thereof in the example, which constitutes a TGC circuit. In FIG. 1, reference numeral 100 indicates an LNA, reference numeral 10 indicates a transducer, and reference numeral 60 indicates a single differential converter. Further, the LNA 100 is constituted of a variable attenuator 20, amplifying circuits 30 and 40, bias current generators 31 and 41, and a subtractor 50, in which reference numerals 32 and 42 indicate bias currents, reference numeral 43 indicates an attenuator control signal, reference numeral 45 indicates an attenuator off command signal, reference numeral 70 indicates an output of the LNA, reference numeral 80 indicates a TGC control signal, and reference numeral 81 indicates a gain control signal. In addition, FIGS. 2A to 2D illustrate timing charts of the TGC control signal 80, the bias currents 32 and 42, and the LNA gain in FIG. 1.

Hereinafter, an operation of the LNA 100 will be described with reference to FIGS. 1 and 2A to 2D. In FIG. 1, a signal converted from an ultrasonic wave to an electric signal by the transducer 10 is input to the variable attenuator 20 via a transmission/reception changeover switch (not illustrated) for protecting the LNA 100 from a large amplitude signal from a transmission circuit (not illustrated). The variable attenuator 20 attenuates the electric signal according to the level of the attenuator control signal 43. The attenuated electrical signal is input to the amplifying circuits 30 and 40.

The amplifying circuit 30 is supplied with the bias current 32 from the bias current generator 31 and the amplifying circuit 40 is supplied with the bias current 42 from the bias current generator 41. The bias current generator 41 can also turn off the attenuation function of the variable attenuator 20 by the attenuator off command signal 45. That is, a signal not attenuated by the attenuator off command signal 45 can be supplied to the amplifying circuits 30 and 40. When the TGC function is used, the variable attenuator 20 is always in an On state (by the means described below, when the TGC is terminated, the variable attenuator 20 is turned off without using the attenuator off command signal 45). The output signals of the amplifying circuits 30 and 40 are subtracted by the subtractor 50 and output from the output 70.

Figure 2A:
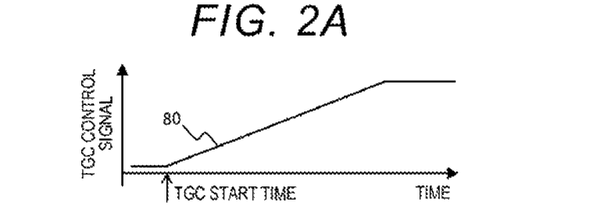
FIGS. 2A to 2D are timing charts of FIG. 1.
Figure 2B:
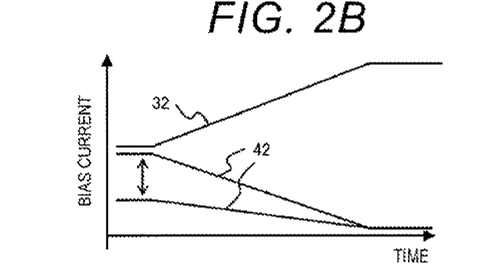

As illustrated in FIG. 2A, the TGC control signal 80 is a ramp-up signal which gradually rises from a time at which the TGC is desired to be started. As illustrated in FIG. 1, the TGC control signal 80 becomes a differential signal by the single differential converter 60 and is input to the bias current generators 31 and 41. The bias current generators 31 and 41 which have received the differential signal generate the bias currents 32 and 42 as illustrated in FIG. 2B. The bias current 42 is designed to be always smaller than the bias current 32 from a time at which the TGC is desired to be started (time when the TGC control signal 80 starts ramping up) to an end time. This is to prevent the polarity of the signal from being reversed when the subtractor 50 subtracts the output signals of the amplifying circuits 30 and 40.

Figure 2C:
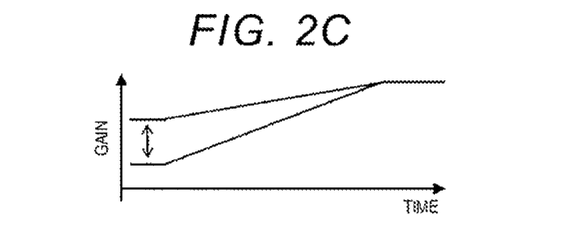

The gain control signal 81 in FIG. 1 realizes the variable gain function of the LNA 100 by varying a current value at the start of the TGC of the bias current 42. As illustrated in FIG. 2C, the gain of the LNA 100 is determined by a difference between the bias currents 32 and 42, and thus the gain variation is carried out by changing the magnitude of the bias current 42 (the bias current 42 is varied as illustrated by arrows in FIGS. 2B and 2C) according to a variable gain range to be set. The variable gain function can be realized without adding parts to the LNA 100 main body to be arranged in a matrix form of the 2D array IC.

Figure 2D:
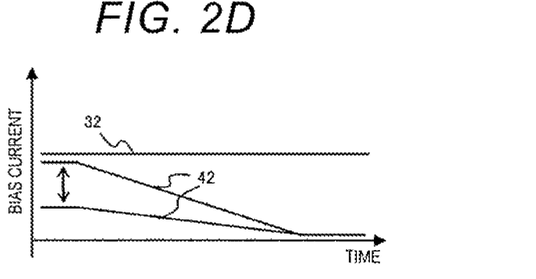

On the contrary, the gain of the amplifying circuit 30 is lower because the bias current 32 at the start of the TGC is smaller than that at the end of the TGC. The electric signal level from the transducer 10 is high at the start of TGC, and thus the gain of the LNA 100 is set low to prevent circuit saturation. Also, since the electric signal level is high at the start of the TGC, the SNR is high, and thus it is set to prevent saturation rather than to make low noise of the amplifying circuit 30. Further, even when a desired attenuation degree of the variable attenuator 20 is set to a low value, a desired gain variable width can be realized, so that the circuit area of the variable attenuator can also be reduced. As a matter of course, as illustrated in FIG. 2D, even with a bias method where the bias current 32 is fixed and does not change, the variable gain function of the LNA 100 can be realized, but the power consumption increases. In the example, the power consumption of the LNA 100 at the start and the end of the TGC can be made substantially constant.

Basically, the amplifying circuits 30 and 40 are manufactured by providing the same circuits on the same chip by semiconductor technology. However, as described below, in a case of being mounted on a 2D array probe in combination with a chip obtained from another lot having different process variation, the gain also has a process variation dependency. In the process in which the gain of the amplifying circuit 30 is lower by 3 dB, the gain of the amplifying circuit 40 is also lower by approximately 3 dB. That is, the relationship of output signal amplitude of LNA 100 is satisfied as follows:

Output signal amplitude of LNA 100=(gain of the amplifying circuit 30+process error of gain of the amplifying circuit 30)×input signal amplitude−(gain of the amplifying circuit 40+process error of gain of the amplifying circuit 40)×input signal amplitude≈(gain of the amplifying circuit 30−gain of the amplifying circuit 40)×input signal amplitude.

Therefore, the level of the output signal obtained by subtracting those output signals with the subtractor 50 has a small process variation dependency.

Figure 3:
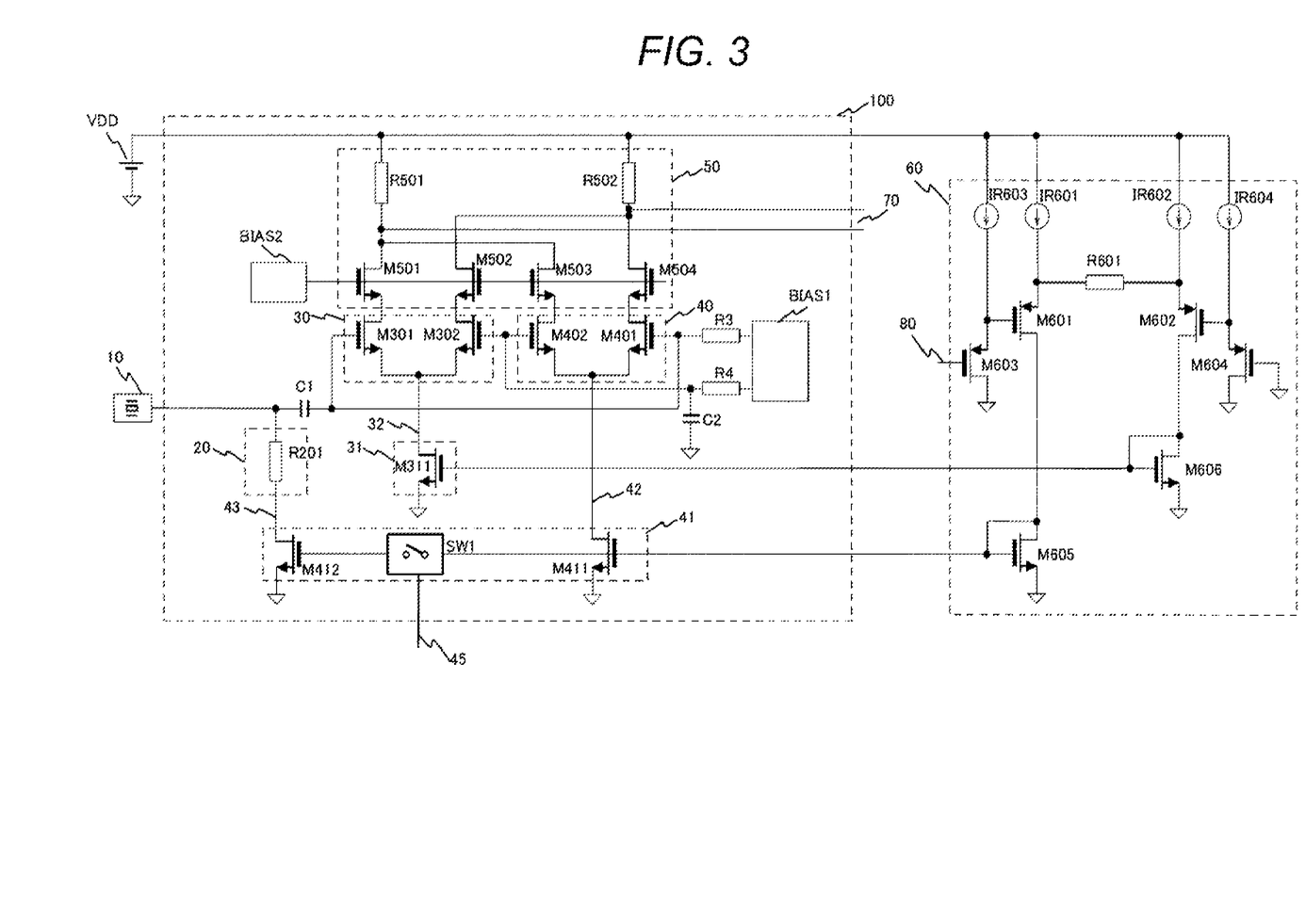
FIG. 3 is a first circuit example of the block configuration diagram of FIG. 1.

FIG. 3 is a first circuit example of the block configuration diagram of FIG. 1. In FIG. 3, the same reference numerals as in FIG. 1 are assigned to components performing the same operations as those in FIG. 1 and the descriptions thereof will be omitted. In FIG. 3, VDD indicates a power supply voltage, M number indicates a MOSFET, R number indicates a resistor, C number indicates a capacitor, SW number indicates a switch, IR number indicates a current source, and BIAS1 and BIAS2 indicate bias voltage supply circuits.

In FIG. 3, the variable attenuator 20 is constituted only of R201, but realizes a variable attenuation degree function by series connection with M412 described below.

The amplifying circuit 30 is a differential amplifying circuit constituted of M301 and M302 and is supplied with the bias current 32 from the bias current generator 31 formed of M311. 311 is a tail current source of the amplifying circuit 30. The amplifying circuit 40 is a differential amplifying circuit constituted of M401 and M402 and is supplied with the bias current 42 from the bias current generator 41 formed of M411. M411 is a tail current source of the amplifying circuit 40.

The gate bias voltages of M301 and M302, M401 and M402 are supplied by the BIAS1 via R3 and R4. In the gates of M301 and M401, the signal obtained by attenuating a signal from the transducer 10 by the variable attenuator 20 is input via C1. The gates of M302 and M402 are grounded alternately to the ground by C2.

The output current signals of the amplifying circuits 30 and 40 are subtracted by the subtractor 50 and output from the output 70.

The subtractor 50 does not realize the subtraction function by cross-coupling connection (connection where the polarity is inverted and current is added) of the output current signals of the amplifying circuits 30 and 40 and realizes the subtraction function by cross-coupling the cascoded MOSFET group output currents through M501 to M504 to which the gate bias voltage is supplied from BIAS2. Since the amplifying circuit 40 is turned off at the end of the TGC, by cascading, positive feedback is prevented from being applied to the amplifying circuit 30 via the unintended parasitic capacitor.

Since the output current signals of the amplifying circuits 30 and 40 are cross-coupled, the amplitude of the large signal output due to the large signal input is also inverted in polarity and is added, whereby saturation of the circuits can be prevented.

The TGC control signal 80 becomes a differential signal current by a single differential converter constituted of M601 to M604, R601, and IR601 to IR604 and is supplied to M605 and M606. M606 and M311, M605 and M411 are respectively current mirror circuits. Therefore, in the bias current which becomes the differential signal current in the single differential converter 60, a current proportional to the current of M606 in the bias current generator 31 is converted into the bias current 32 by M311 and a current proportional to the current of M605 in the bias current generator 41 is converted into the bias current 42 by M411. Therefore, also in the circuit example of FIG. 3, the bias current generators 31 and 41 generate the bias currents 32 and 42 as illustrated in FIG. 2B.

The gate voltages of M411 and M412 are both supplied from M605. Therefore, the gate voltage is converted, by M412, into the attenuator control signal 43 which decreases with the elapse of time similar to that of the bias current and the variable attenuator 20 realizes a variable function of decreasing the attenuation degree with the elapse of time by the series connection of R201 and M412. That is, it is possible to control the attenuation degree of the attenuator by voltage-dividing the signal by the output impedance of the transducer 10 and an on-resistor of transmission/reception changeover switch (not illustrated), and R201 and M412.

Also, since the gate voltages of M411 and M412 are both supplied from M605, when the gate voltage of M411 becomes the ground level and the bias current 42 becomes zero, and further the amplifying circuit 40 is turned off, simultaneously the gate voltage of the M412 also becomes the ground level. As a result, at the end of the TGC when the variable attenuator 20 of which the attenuation degree is determined by the series resistors of R201 and M412 is turned off, the LNA 100 operates as a high-gain and low-noise amplifying circuit which operates as an amplifying circuit 30 alone.

Figure 4:
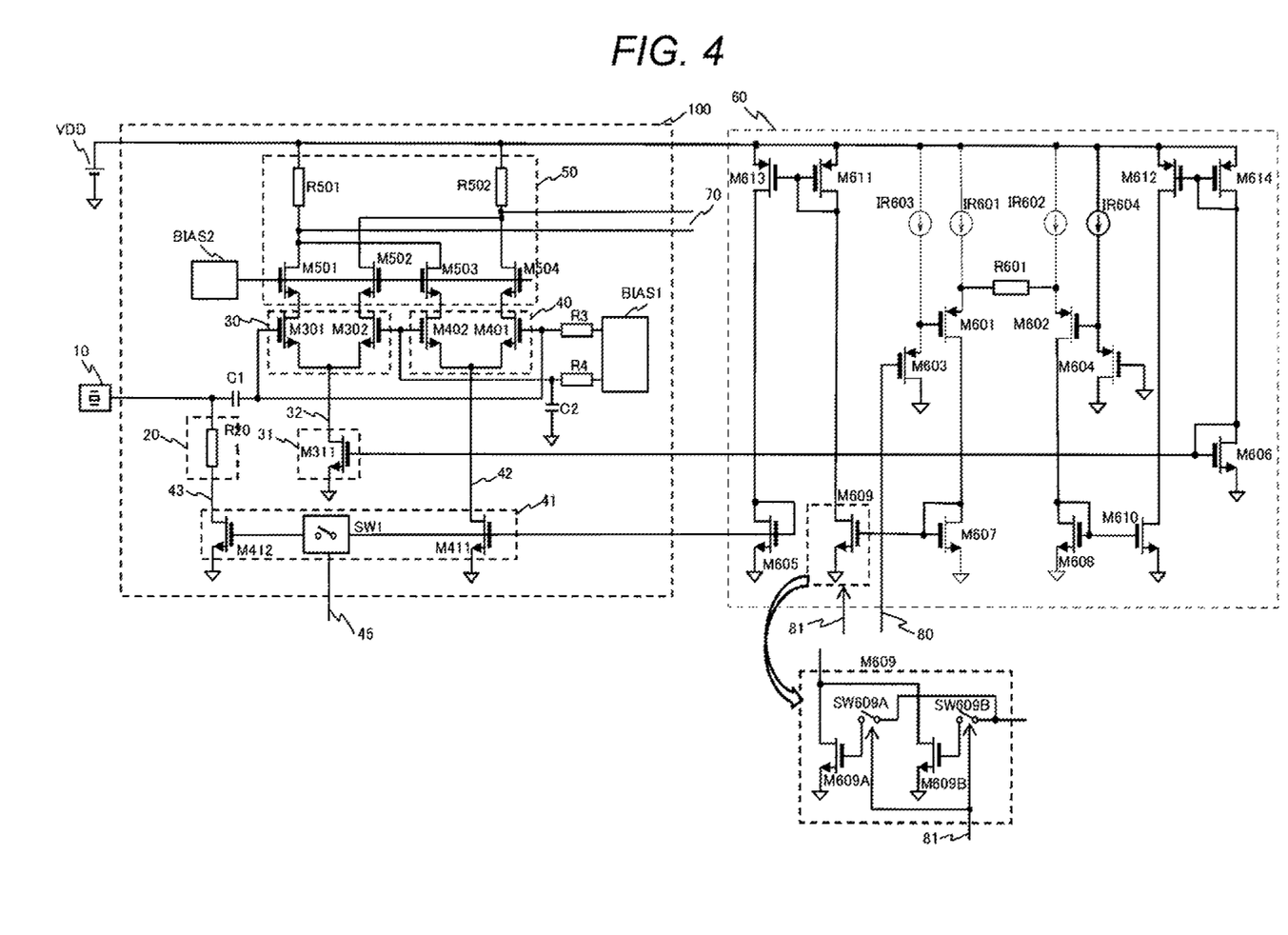
FIG. 4 is a second circuit example of the block diagram of FIG. 1.

FIG. 4 is a second circuit example of the block diagram of FIG. 1. In FIG. 4, the same reference numerals as those in FIG. 3 are assigned to components performing the same operations as those in FIG. 1 and the descriptions thereof will be omitted. In FIG. 4, the difference from FIG. 3 is that the variable gain function of the LNA 100 is realized by the gain control signal 81.

In FIG. 4, the TGC control signal 80 becomes a differential signal current by a single differential converter constituted of M601 to M604, R601, and IR601 to IR604 and is supplied to M607 and M608.

M607 and M609, M608 and M610 are respectively current mirror circuits. The ratio of the drain currents of M608 and M609 is constant. However, as illustrated in an auxiliary figure at the bottom of FIG. 4, in M609, the ratio of drain current flowing in M607 to drain current flowing in M609 can be varied by the gain control signal 81 while switching MOSFET arrays having different sizes with switches.

The gain control signal 81 realizes the variable gain function of the LNA 100 by varying the current value at the start of the TGC of the bias current 42. Since the gain of the LNA 100 is determined by the difference between the bias currents 32 and 42, the gain is varied by changing the magnitude of the bias current 42 according to the variable gain range to be set. As a result, the variable gain function can be realized without adding parts to the LNA 100 main body to be arranged in a matrix form of the 2D array IC.

The drain current of M610 is supplied to M606 by a current mirror circuit constituted of M612 and M614 and the drain current of M609 is supplied to M605 by a current mirror circuit constituted of M611 and M613.

As described above, according to the example, it is possible to realize LNAs each having the variable gain function with one independent small-variation for each transducer array of several thousands to ten thousand elements and to perform TGC control while reducing the circuit size in a state where a large number of LNAs are arranged in a 2D array form. As a result, it is possible to provide an ultrasonic diagnostic apparatus including a 2D array probe improved in SNR of near and deep diagnostic images.

EXAMPLE 2

Figure 5:
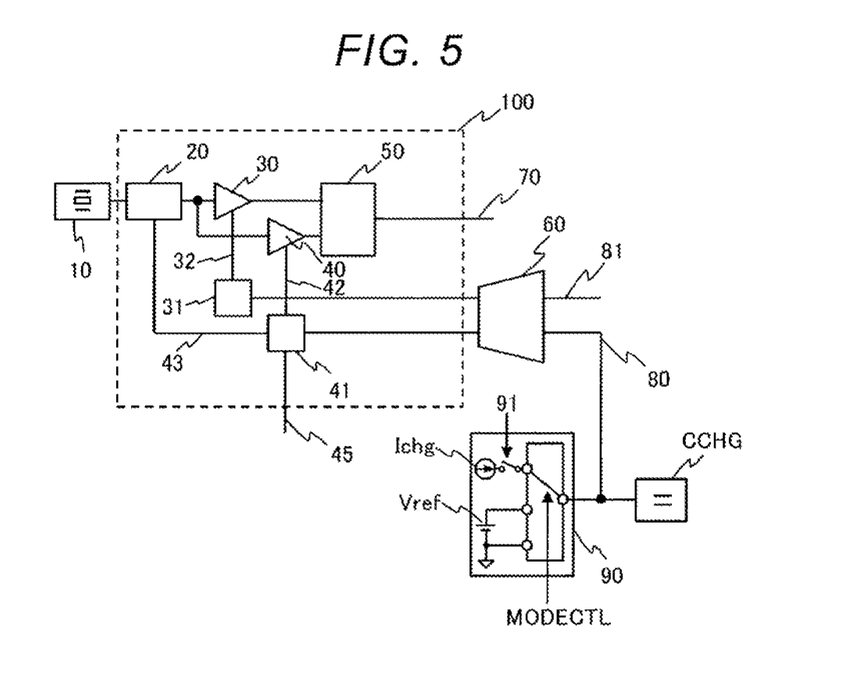
FIG. 5 is a block configuration diagram of an LNA and the periphery thereof in Example 2.

FIG. 5 is a block configuration diagram of an LNA and the periphery thereof in the example, which constitutes a TGC circuit. In FIG. 5, the same reference numerals are assigned to the same functional parts as those in FIG. 1 and the descriptions thereof will be omitted. In FIG. 5, a difference from FIG. 1 is that a generation circuit for the TGC control signal 80 is added.

In FIG. 5, a charge/discharge current generator 90 and a capacitor CCHG are connected and the TGC control signal 80 is generated from the connection point.

In the charge/discharge current generator 90, Ichg is the current source and Vref is the power supply. In addition, a mode in which a constant current is supplied to the capacitor CCHG by a MODECTL signal and a mode in which the TGC control signal 80 is set to a high level (power supply potential) or a low level (ground potential) are provided. In addition, in the mode in which the constant current is supplied to the capacitor CCHG, the timing at which the constant current is supplied to the capacitor CCHG is determined by a timing signal 91. Also, the current source Ichg can vary the constant current value.

Figure 6A:
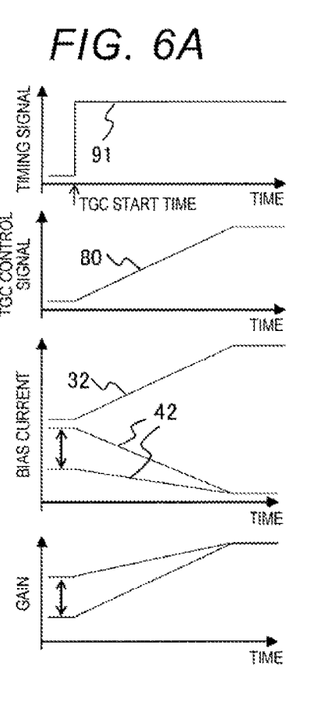
FIGS. 6A to 6C are timing charts of FIG. 5.
Figure 6B:
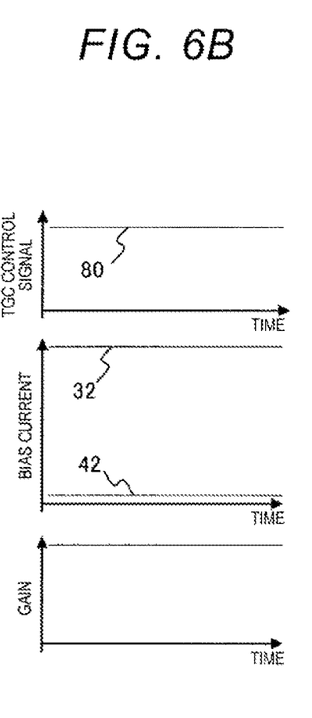
Figure 6C:
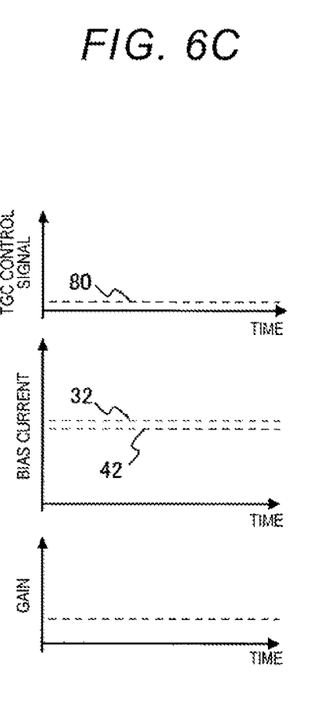

FIGS. 6A to 6C illustrate timing charts of the timing signal 91, the TGC control signal 80, the bias currents 32 and 42, and the LNA gain in FIG. 5. FIG. 6A illustrates a mode in which a constant current is supplied to the capacitor CCHG by the MODECTL signal and FIG. 6B illustrates a mode in which the TGC control signal 80 is set to a high level, and further FIG. 6C illustrates a mode in which the TGC control signal 80 is set to a low level.

First, in the mode in which the constant current is supplied to the capacitor CCHG as illustrated in FIG. 6A, the current source Ichg is connected by raising the timing signal 91 from the TGC start time, and then, a ramp-up waveform as illustrated in FIG. 6A can be generated as the TGC control signal 80 by supplying the constant current to the capacitor CCHG from the TGC start time. The ramp-up waveform of the TGC control signal 80 is saturated with the power supply voltage for operating the charge/discharge current generator 90, which is the TGC end time and provides the maximum gain to the LNA 100. When the reception is completed and the succeeding TGC operation is performed, the charge of the CCHG is discharged.

In a case of a diagnosis mode that does not use the TGC such as pulse Doppler, the current output of the charge/discharge current generator 90 is turned off and the mode is switched to a mode for outputting a high level (power supply potential) or a low level (ground potential) as the TGC control signal 80. In a case of the high level, as illustrated in FIG. 6B, the LNA 100 has the maximum gain and operates as a fixed gain amplifier. On the contrary, in a case of the low level, as illustrated in FIG. 6C, since the amplifying circuit 40 is turned on, the LNA 100 has a low gain and operates as a fixed gain amplifier. However, even at the low level, the gain can be varied by changing the magnitude of the bias current 42 by the gain control signal 81.

EXAMPLE 3

Figure 7:
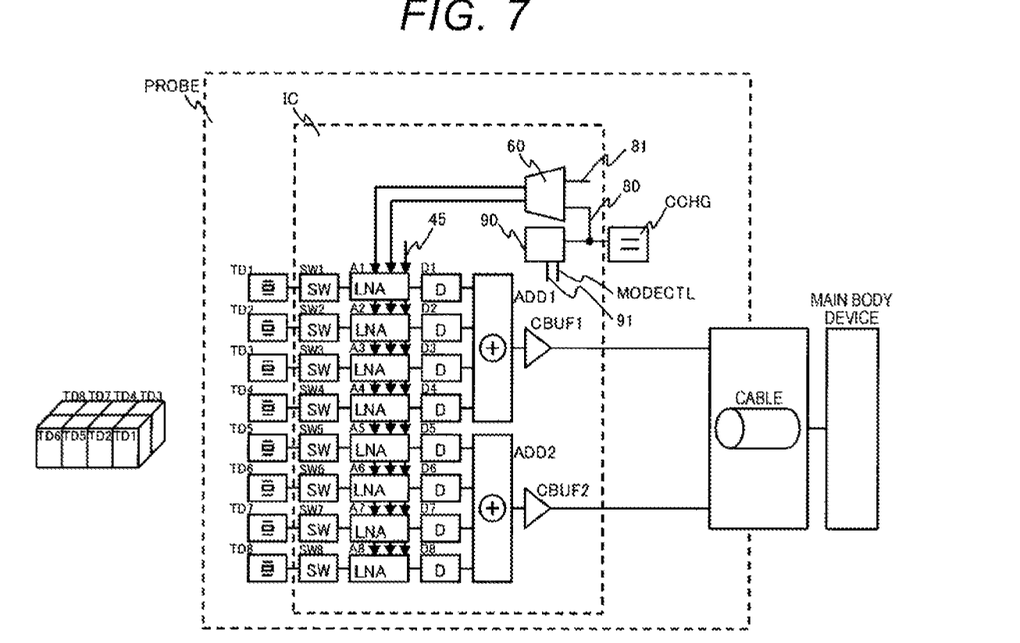
FIG. 7 is a first block configuration diagram when a large number of LNAs are mounted on a 2D array IC according to Example 3.

FIG. 7 is a first block configuration diagram when a large number of LNAs described in Examples 1 and 2 are mounted on the 2D array IC in the example. In FIG. 7, the same reference numerals are assigned to the same functional parts as those in FIG. 1 and FIG. 5 and the descriptions thereof will be omitted. In FIG. 7, an IC indicates a 2D array IC, PROBE indicates a 2D array probe, TD1 to TD8 indicate transducers, SW1 to SW8 indicate transmission/reception changeover switches, A1 to A8 indicate LNAs, D1 to D8 indicate delay circuits, ADD1 to ADD2 indicate adder circuits, and CBUF1 and CBUF2 indicate buffer circuits, and further a cable and a main unit are provided.

In FIG. 7, in the 2D array probe PROBE, transducers are arranged in a matrix form as illustrated by the transducers TD1 to TD8 on the left side. In FIG. 7, there are eight transducers in total, four in a long axis direction and two in a short axis direction. One independent transmission/reception circuit mounted on the 2D array IC corresponds to each of the transducers TD1 to TD8.

In FIG. 7, a transmission circuit (not illustrated), the transmission/reception changeover switch SW, the LNA, and the delay circuit D correspond to the independent transmission/reception circuit.

The signal converted from the ultrasonic wave to the electric signal by the transducer TD1 is input to the LNA-A1 via the transmission/reception changeover switch SW1 (Since the switch is in reception, the switch is turned on and connected with low impedance) for protecting the LNA from a large amplitude signal from the transmission circuit (not illustrated). With this signal LNA-A1, the SNR is amplified without deterioration as much as possible while avoiding the saturation by the TGC means described in Examples 1 and 2, and the amplified SNR is input to the delay circuit D1. The amplified SNR passes through the delay circuit D1, is delayed for a desired time, and then is input to the adder circuit ADD1.

Similarly, the signals converted from the ultrasonic waves to the electric signals by the transducers TD2 to TD4 pass through the LNA-As and the delay circuits D and are input to the adder circuit ADD1. The adder circuit ADD1 adds those signals, and the signals are power-amplified by the buffer circuit CBUF1, drive the cable, and are sent to the main unit.

During transmission, the adder circuit ADD1 (not illustrates) branches the same transmission signal to the delay circuits D1 to D4. The branched signals are delayed by a desired time in the delay circuits D1 to D4 and drive transducers respectively connected thereto via transmission circuits (not illustrated). During transmission, the transmission/reception changeover switch for protecting the LNA-A from the large amplitude signal from the transmission circuit is turned off and connected to the LNA-A with high impedance. There is no switch in particular between a transmission circuit constituted using a high breakdown voltage transistor and a transducer. Electric signals by the transducers TD5 to TD8 are also processed in a similar way.

The delay time set for the delay circuits D1 to D8 is set such that a distance, for example, from a target focal point to the center of the transducer group is calculated and the transmission/reception circuit arranged at the shortest distance transmits and receives at the latest time. That is, a pseudo lens operation is performed using the 2D array IC.

The attenuator off command signal 45 turns off the variable attenuator attenuation function of the LNA-A, but the attenuator off command signal 45 is shared by the transmission/reception circuits of eight paths.

As illustrated in FIG. 6A, the TGC control signal 80 a signal that gradually rises from the time when the TGC is to be started. The TGC control signal 80 becomes a differential signal by the single differential converter and is input to the bias current generator of the LNA-A, but the differential signal is shared by the transmission/reception circuits of eight paths.

As explained in FIGS. 3 and 4, M606 and M311, M605 and M411 are respectively current mirror circuits. Therefore, in FIG. 7, eight LNA-As are arranged and the gates of M311 and M411 of each are short-circuited at the same time. Therefore, the same current can flow through the amplifying circuits 30 and 40 of the LNA-A1 to LNA-A8. That is, it is possible to perform TGC control of eight LNAs with two wires.

The gain control signal 81 realizes the variable gain function of the LNA-A by changing the current value at the TGC start time of the amplifying circuit 40 of the LNA-A1 to LNA-A8. Since the variable gain function can be realized without adding parts to LNA-A1 to LNA-A8, a silicon area of each LNA can be reduced.

Figure 8:
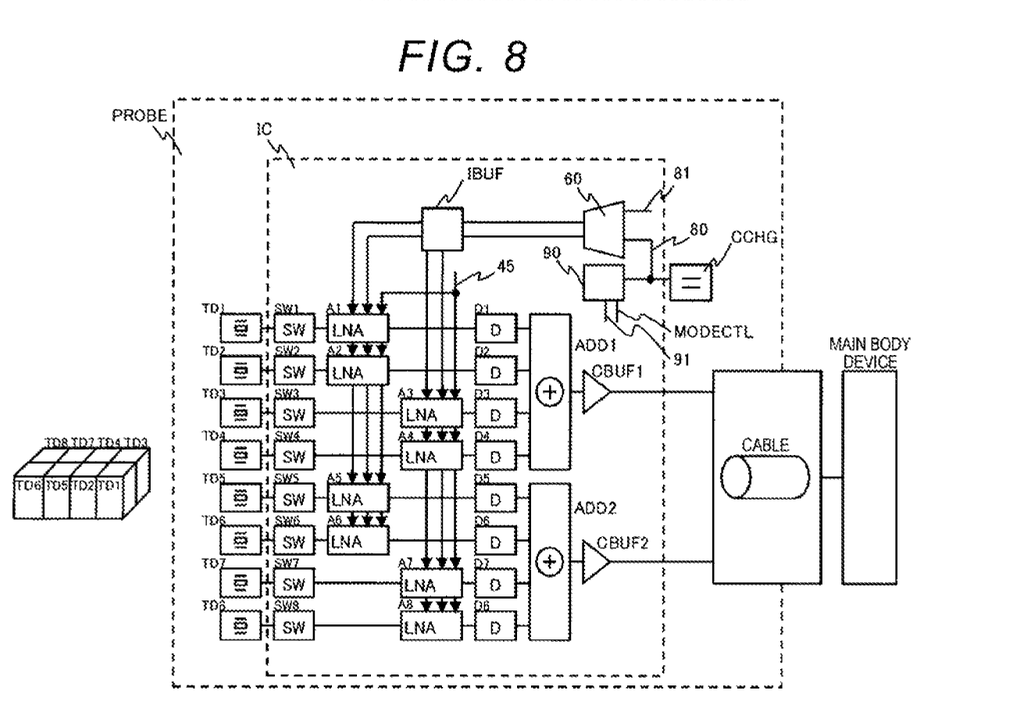
FIG. 8 is a second block configuration diagram when a large number of LNAs are mounted on the 2D array IC according to Example 3.

FIG. 8 is a second block configuration diagram when a large number of LNAs described in Examples 1 and 2 are mounted on the 2D array IC in the example, similar to the case of FIG. 7. In FIG. 8, the same reference numerals are assigned to the same functional parts as those in FIG. 7 and the descriptions thereof will be omitted.

In FIG. 8, the IBUF is a buffer circuit. Further, the TGC control signal 80 becomes a differential signal by the single differential converter 60 and is input to the bias current generator of the LNA-A. However, the differential signal is once converted from the differential voltage to the differential current by the buffer circuit IBUF and output again as the differential voltage. The input voltage to the bias current generator of the LNA-A does not change before and after the input of the buffer circuit IBUF and has a role of reducing the influence of long-distance wiring.

In FIG. 8, the wiring to be laid out in the long axis direction of the transducer array on the left side is shared by the transmission/reception circuits of four paths. In FIG. 8, there are eight transducers. However, for example, in a case of performing TGC control of 2,048 LNAs in total, 64 LNAs in the long axis direction and 32 LNAs in the short axis direction, by arranging 32 IBUFs referring to FIG. 8, it is possible to perform TGC control of 2,048 LNAs by one TGC control signal 80 by merely sharing only 64 differential voltages in the long axis direction.

Figure 9:
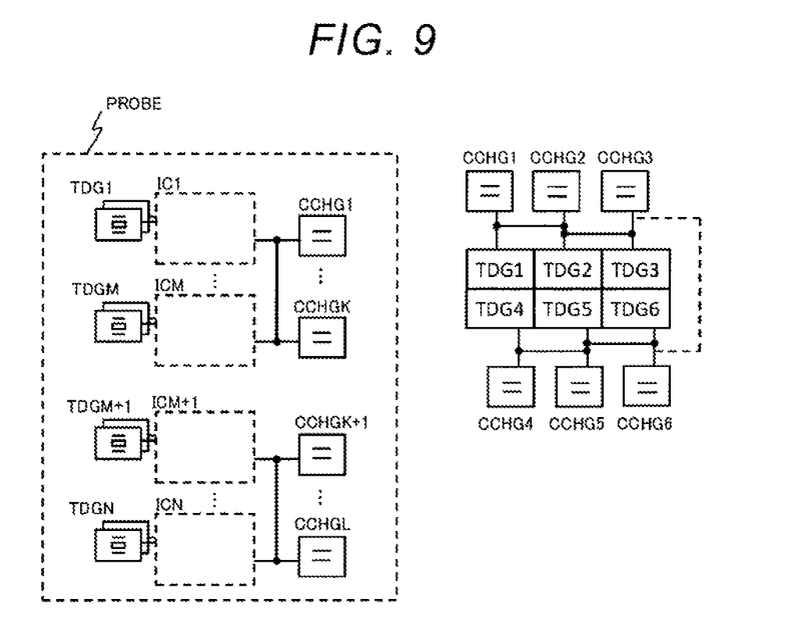
FIG. 9 is a block configuration diagram when a plurality of 2D array ICs are mounted in a 2D array probe according to Example 3.

FIG. 9 is a block configuration diagram when a plurality of 2D array ICs are mounted in the 2D array probe. In FIG. 9, IC1 to ICN indicate 2D array ICs (M≤N), PROBE indicates a 2D array probe, CCHG1 to CCHGL indicate capacitors (K≤L), and TDG1 to TDGN indicate transducer groups (M≤N).

Each of the transducer groups TDG1 to TDGN (M≤N) is constituted of P transducers and is mounted in a matrix form in the 2D array probe PROBE. For example, the case of N=6 is illustrated on the right side in FIG. 9. The 2D arrays IC1 to ICN are respectively connected to the transducer groups TDG1 to TDGN having the same number. Since the 2D arrays IC1 to ICN each has unique process variations, as illustrated in FIG. 5, the values of the constant currents flowing from the charge/discharge current generator 90 from the TGC start time are different. In addition, the capacitor CCHG also has variations as individual parts. Therefore, assuming that the capacitor CCHG connected respectively is charged from each 2D array IC as illustrated in FIGS. 7 and 8, if a clock (not illustrated) supplied to the 2D array IC is common, the TGC start time can be synchronized in N chips, but the TGC end time will vary.

Therefore, in FIG. 9, some K CCHGs are shared by the IC1 to ICM and the TGC control signal 80 is shared. By outputting the same charging current from M ICs and also short-circuiting CCHG1 to CCHGK for sharing, variations in the charging currents and variations in the CCHGs are averaged, and thus variations in the TGC end times can be reduced in IC1 to ICM. ICM+1 to ICN and the CCHGK+1 to CCHGL are also similar.

When all 2D array ICs share CCHGs, it is possible to reduce the variation in TGC end times within the 2D array probe. However, for example, when adopting the 2D array IC arrangement as illustrated in the right side of FIG. 9, connecting a dotted line results in a wiring loop, which is susceptible to electromagnetic noise. Therefore, the dotted line is not connected, CGHGs are divided into two vertically and the variation of the TGC end time is reduced only in three 2D array ICs in the upper and lower sides. Although the TGC end times slightly differ between the upper and lower sides, the variation of the TGC end time is reduced to $1/\sqrt{(3)}$ by the standard deviation as compared with the independent TGC control in the six 2D array ICs.

Figure 10:
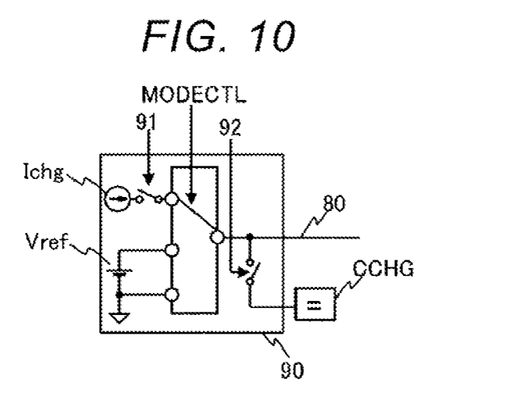
FIG. 10 is a configuration diagram for explaining time variation from a TGC start time to an end time in Example 3.

When mounting a plurality of 2D array ICs in the 2D array probe as illustrated in FIG. 9, by switching the plurality of existing capacitors CCHGs with the switch, the time from the TGC start time to the end time can be varied. A block diagram for realizing the above is illustrated in FIG. 10.

By adding switches and a capacitor connection control signal 92 to the charge/discharge current generator 90, the capacitor CCHG can be connected to and disconnected from the TGC control signal 80. As a result, the TGC period can be varied. As a matter of course, even when there is only one 2D array IC, a similar TGC period variable function can be realized by providing an independent terminal connecting the capacitors CCHGs.

EXAMPLE 4

Figure 11:
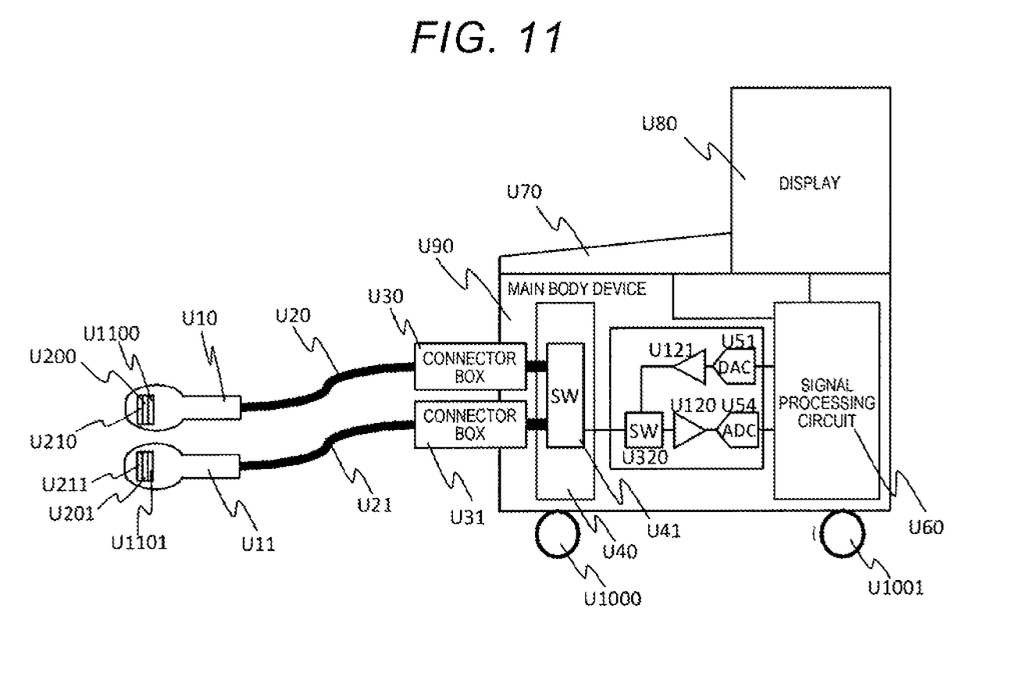
FIG. 11 is a configuration diagram of an ultrasonic diagnostic apparatus according to Example 4.

FIG. 11 is a configuration diagram of an ultrasonic diagnostic apparatus according to the example. In FIG. 11, U10 and U11 indicate 2D array probes, U20 and U21 indicate cables, U30 and U31 indicate connector boxes, U40 indicates a probe selector, U41 indicates a probe changeover switch, U120 and U121 indicate amplifiers, U51 indicates a digital-to-analog converter, U320 indicates a switch, U54 indicates an analog-to-digital converter, U60 indicates a signal processing circuit, U70 indicates an operation panel, U80 indicates a display, U90 indicates a main unit, U1100 and U1101 indicate 2D array ICs, U200 and U201 indicate matching layers, U210 and U211 indicate acoustic lenses, and U1000 and U1001 indicate casters.

The 2D array ICs of Example 3 corresponds to U1100 and U1101. The main unit U90 has two connector boxes U30 and U31 and two 2D array probes U10 and U11 are connected via the cables U20 and U21, but the number is not limited to two. In addition, 1D array probes of the related art or the like can be connected to the connector boxes U30 and U31. There is also a device provided with a connector box connection terminal for connecting a special probe such as for Doppler only. The main unit U90 is freely movable on a floor surface by the casters U1000 and U1001.

For the circuit, switching between the 2D array probe U10 and the 2D array probe U11 is carried out with a probe selector U40 and a probe changeover switch U41.

The 2D array IC-U1100 and U1101 are respectively built in the inside of the 2D array probes U10 and U11. A 2D array transducer (not illustrated) is connected to a surface on which an external terminal connection portion of the 2D array IC-U1100 is mounted. As described above, the 2D array probe is constituted of several thousands to ten thousand transducers mounted in an array form. The 2D array IC-U1100 is equipped with the 2D array transducer, the matching layer U200 for matching the acoustic impedance of the living body, and the acoustic lens U210 for converging the ultrasonic beams so that ultrasonic waves can be efficiently transmitted and received. Similarly, the 2D array transducer, the matching layer U201, and the acoustic lens U211 are mounted on the 2D array U1101.

The amplifier U121 serves to amplify the transmission signal, the switch U320 functions to prevent the transmission signal from entering the reception system, and the amplifier U120 amplifies the reception signal. The signal processing circuit U60 is a logic circuit and inputs the signal of the amplifier U120 as a digital signal via the analog-to-digital converter U54 to perform signal processing. Further, the signal-processed signal is input to the amplifier U121 via the digital-to-analog converter U51 and the signal is transmitted to the 2D array probes U10 and U11 via the probe selector U40, the connector boxes U30 and U31, and the cables U20 and U21.

Various operations of the main unit U90 such as which part in the body of a patient is viewed are performed from the operation panel U70. In addition, the main unit U90 includes various diagnostic modes and switching of the diagnostic mode is also performed from the operation panel U70. Diagnostic modes include Brightness (B), Pulsed Wave Doppler (PW), Color Flow Mapping (CFM), Steerable CW Doppler (STCW) modes and the like. The B mode is a mode in which the received amplitude intensity of the ultrasonic wave reflected from the tissue is displayed in association with the brightness and the PW mode is a mode for repeatedly transmitting the ultrasonic wave toward a certain depth and measuring the frequency deviation for each repetitive transmission of the signal reflected from the part to obtain the blood flow velocity. Further CFM, also called color Doppler, is a mode for visualizing the blood flow velocity by obtaining the autocorrelation of the reception signal for each ultrasound transmission. The STCW mode is also a mode for measuring the blood flow velocity, which is suitable for fast blood flow velocity measurement. In the PW mode, the blood flow velocity at a specific position can be known and can be displayed in a state of being superimposed on the B mode image. In the CFM mode, the average speed in positions at multiple points on an ultrasonic reception beam is known and is used for discovering backflow or the like.

The signal processing circuit U60 processes the signal from the analog-to-digital converter U54 and obtains diagnostic images of the various modes described above. The diagnostic image is displayed on the display U80.

The TGC circuit in the example is not limited to the 2D array IC and can be used for reception of ultrasonic signals by a normal ultrasonic probe such as 1D. Also, even when the TGC circuit is mounted on a device side instead of the probe, the equivalent TGC function can be realized.

Hereinbefore, the examples are described. However, the invention is not limited to the examples described above and includes various modifications. For example, the examples described above are described in detail in order to explain the invention in an easy-to-understand manner and are not necessarily limited to those having all the configurations described.

What is claimed is:

1. A probe used for an ultrasonic diagnostic apparatus, the probe configured to transmit an ultrasonic wave to a diagnostic site, receive a reception signal which is a reflected wave and obtain information necessary for diagnosis based on the reception signal, the probe comprising:
   a plurality of transducers;
   a plurality of low-noise amplifying circuits each corresponding to one of the plurality of transducers; and
   a single differential converter which converts a control signal rising with an elapse of time to a first bias signal rising with the elapse of time and a second bias signal falling with the elapse of time to control the plurality of low-noise amplifying circuits, wherein
   each of the low-noise amplifying circuits includes
   an attenuator which attenuates an electric signal from a respective transducer of the plurality of transducers,
   a first amplifying circuit which sets the first bias signal as a bias and amplifies an output signal of the attenuator to be gradually increased with the elapse of time,
   a second amplifying circuit which sets the second bias signal as a bias and amplifies the output signal of the attenuator to be gradually reduced with the elapse of time, and
   a subtractor which subtracts an output of the first amplifying circuit and an output of the second amplifying circuit;
   the first amplifying circuit and the second amplifying circuit are first and second cascode-connected differential amplifying circuits and realize the subtractor by being connected after switching polarities of respective outputs;
   the attenuator is constituted by series-connecting a resistor and a transistor; and
   a bias voltage of the tail current source of the second cascode-connected differential amplifying circuit and a bias voltage of the transistor constituting the attenuator are shared.

2. The probe according to claim 1, wherein during an operation period, the first bias signal is always greater than the second bias signal.

3. The probe according to claim 1, wherein using the second bias signal, an attenuation degree of the attenuator is reduced with the elapse of time.

4. The probe according to claim 1, further comprising:
a constant current generation circuit for generating the control signal by charging a capacitor with a constant current.

5. The probe according to claim 4, wherein
the constant current generation circuit has a function of discharging the capacitor and a function of fixing the capacitor to a power supply voltage.

6. The probe according to claim 4, wherein
the constant current generation circuit has a function capable of disconnecting the capacitor.

7. The probe according to claim 4, wherein
the constant current generation circuit has a function capable of varying a constant current value for charging the capacitor.

8. The probe according to claim 1, wherein
the first bias signal is constant during the elapse of time.

9. The probe according to claim 1, wherein
the single differential converter can vary a gain by varying the second bias signal.

10. The probe according to claim 1, wherein
a signal not attenuating with the attenuator turned off is supplied to the first amplifying circuit and the second amplifying circuit.

11. The probe according to claim 1, wherein
the first amplifying circuit and the second amplifying circuit can be used as fixed gain amplifiers.

12. The probe according to claim 1, wherein
the first bias signal and the second bias signal are respectively tail current sources of the first and second cascode-connected differential amplifying circuits.

13. The prove according to claim 1, wherein
the single differential converter and the plurality of low-noise amplifying circuits are constituted of one semiconductor circuit and the plurality of low-noise amplifying circuits are commonly controlled by the first bias signal and the second bias signal in the single differential converter.

14. The probe according to claim 1, wherein
the single differential converter and the plurality of low-noise amplifying circuits are constituted of a plurality of semiconductor circuits and the plurality of low-noise amplifying circuits are commonly controlled by the first bias signal and the second bias signal in the single differential converter, and
the control signal is shared by the plurality of semiconductor circuits.

15. An ultrasonic diagnostic apparatus comprising:
a probe for transmitting an ultrasonic wave to a diagnostic site and receiving a reception signal which is a reflected wave; and
a signal processing circuit for obtaining information necessary for diagnosis based on the reception signal, wherein
the probe includes a plurality of transducers, a plurality of low-noise amplifying circuits respectively corresponding to the plurality of transducers, and a single differential converter which converts a control signal rising with the elapse of time to a first bias signal rising with the elapse of time and a second bias signal falling with the elapse of time to control the plurality of low-noise amplifying circuits, and
each of the low-noise amplifying circuits includes
an attenuator which attenuates an electric signal from a respective transducer of the plurality of transducers,
a first amplifying circuit which sets the first bias signal as a bias and amplifies an output signal of the attenuator to be gradually increased with the elapse of time,
a second amplifying circuit which sets the second bias signal as a bias and amplifies the output signal of the attenuator to be gradually reduced with the elapse of time, and
a subtractor which subtracts an output of the first amplifying circuit and an output of the second amplifying circuit;
the first amplifying circuit and the second amplifying circuit are first and second cascode-connected differential amplifying circuits and realize the subtractor by being connected after switching polarities of respective outputs;
the attenuator is constituted by series-connecting a resistor and a transistor; and
a bias voltage of the tail current source of the second cascode-connected differential amplifying circuit and a bias voltage of the transistor constituting the attenuator are shared.

* * * * *